(12) United States Patent
Bockenhelmer et al.

(10) Patent No.: US 8,490,473 B2
(45) Date of Patent: Jul. 23, 2013

(54) PRODUCTION METHOD OF A SENSOR FILM

(75) Inventors: Clemens Bockenhelmer, Bremen (DE); Peter Kohl, Riegelsberg (DE)

(73) Assignee: Airbus Deutschland GmbH (DE)

( * ) Notice: Subject to any disclaimer, the term of this patent is extended or adjusted under 35 U.S.C. 154(b) by 813 days.

(21) Appl. No.: 12/444,727

(22) PCT Filed: Oct. 18, 2007

(86) PCT No.: PCT/EP2007/009052
§ 371 (c)(1),
(2), (4) Date: Dec. 2, 2009

(87) PCT Pub. No.: WO2008/046627
PCT Pub. Date: Apr. 24, 2008

(65) Prior Publication Data
US 2010/0071447 A1  Mar. 25, 2010

Related U.S. Application Data

(60) Provisional application No. 60/853,195, filed on Oct. 20, 2006.

(30) Foreign Application Priority Data

Oct. 20, 2006  (DE) .................. 10 2006 049 607

(51) Int. Cl.
*G01N 19/08* (2006.01)
*G01B 5/28* (2006.01)
*B05D 3/12* (2006.01)
*B23C 3/00* (2006.01)

(52) U.S. Cl.
USPC ............................ 73/104; 73/105; 409/131

(58) Field of Classification Search
USPC ............... 73/37, 104, 105; 409/131; 427/490
See application file for complete search history.

(56) References Cited

U.S. PATENT DOCUMENTS

| 2,660,053 | A | * | 11/1953 | Buehner | 73/40 |
| 2,694,924 | A | * | 11/1954 | Matlock et al. | 73/37 |
| 3,483,144 | A | * | 12/1969 | Irving et al. | 279/51 |
| 3,994,763 | A | * | 11/1976 | Sheath et al. | 156/182 |
| 4,002,055 | A | * | 1/1977 | Kops | 73/40 |
| 4,104,906 | A | * | 8/1978 | Oertle | 73/104 |

(Continued)

FOREIGN PATENT DOCUMENTS

DE   60201017 T2   8/2005
DE   102004057290   9/2005

(Continued)

OTHER PUBLICATIONS

Situma et al., "Merging Microfluidics with Microarray-Based Bioassays" Biomolecular Engineering, 23: 213-231 (2006).

(Continued)

*Primary Examiner* — Daniel Larkin
(74) *Attorney, Agent, or Firm* — Lerner, David, Littenberg, Krumholz & Mentlik, LLP

(57) ABSTRACT

The present invention relates to a production method for producing a sensor film for measuring cracks of a material surface using the comparative vacuum measurement method. A gallery having a predetermined gallery course is milled along a surface of the sensor film using a milling apparatus. The sensor film comprises a plastic material.

21 Claims, 5 Drawing Sheets

U.S. PATENT DOCUMENTS

| | | | | |
|---|---|---|---|---|
| 4,145,915 A | * | 3/1979 | Oertle et al. | 73/37 |
| 4,680,442 A | * | 7/1987 | Bauer et al. | 219/121.67 |
| 4,976,136 A | * | 12/1990 | Willan | 73/40.7 |
| 5,404,747 A | * | 4/1995 | Johnston et al. | 73/40 |
| 5,770,794 A | * | 6/1998 | Davey | 73/37 |
| 6,443,041 B1 | * | 9/2002 | Pirovano et al. | 82/56 |
| 6,539,776 B2 | * | 4/2003 | Davey | 73/37 |
| 6,615,642 B2 | * | 9/2003 | Poblete | 73/37 |
| 6,715,365 B2 | * | 4/2004 | Davey | 73/799 |
| 2004/0031558 A1 | | 2/2004 | Johnck | |
| 2004/0094418 A1 | | 5/2004 | Cox et al. | |
| 2008/0264177 A1 | | 10/2008 | Bockenheimer et al. | |

FOREIGN PATENT DOCUMENTS

| | | |
|---|---|---|
| DE | 69732935 T2 | 2/2006 |
| DE | 102006018049 | 10/2007 |
| JP | 2003291576 A | 10/2003 |
| JP | 2003532105 A | 10/2003 |
| WO | 98/00705 | 1/1998 |
| WO | 01/84102 | 11/2001 |
| WO | 01/98746 | 12/2001 |
| WO | 02/40181 | 5/2002 |
| WO | 2005/059522 | 6/2005 |

OTHER PUBLICATIONS

Snakenborg et al., "Direct Milling and Casting of Polymer-based Optical Waveguides for Improved Transparency in the Visible Range", Journal Micromech. Microeng., 16; 375-381 (2006).

Friedrich et al.,"Micromilling Development and Applications for Microfabrication", Microelectronic Engineering, 35; 367-372 (1997).

* cited by examiner

PRODUCTION METHOD OF A SENSOR FILM

REFERENCE TO RELATED APPLICATIONS

This application claims the benefit of the filing date of U.S. Provisional application No. 60/853,195 filed 20 Oct. 2006, and of German patent application 10 2006 049 607.8 filed 20 Oct. 2006, the disclosures of which are hereby incorporated herein by reference.

TECHNICAL AREA

The present invention relates to a method for producing a sensor film for measuring cracks of a material surface using the comparative vacuum measurement method, a sensor film for measuring cracks of a material surface using the comparative vacuum measurement method, a testing method for testing surface cracks of a component using the comparative vacuum measurement method, a usage of a sensor film for measuring cracks of a material surface, and an aircraft having a sensor film for measuring cracks of a material surface using the comparative vacuum measurement method.

BACKGROUND OF THE INVENTION

In aircrafts, it is necessary because of high safety requirements to check the state of the structure of an aircraft. For example, if cracks or fractures arise in the structure and/or in a structure surface, this must be recognized and repair measures must be initiated if necessary.

One possibility for examining crack formation in components is offered by, in addition to conventional nondestructive testing (NDT), the structural health monitoring (SHM) method, which is known in professional circles. The structural health monitoring method is understood as monitoring of components using permanently integrated sensors. In contrast, in conventional NDT, the sensors are removed from the component surface again after the testing. Because of the permanently integrated sensors, more rapid structural monitoring is achieved with the aid of SHM than with conventional NDT, which results in reduced maintenance costs and increased availability of an aircraft.

One technology of SHM is comparative vacuum measurement (CVM) method, which is known in professional circles. A sensor substrate or a sensor film has various air and vacuum channels, the so-called galleries, the air galleries having an atmospheric pressure and the vacuum galleries having a partial vacuum or a vacuum atmosphere. The sensor film is glued onto a component to be tested. If a crack arises on the surface below the CVM sensor during the operation of the aircraft structure, air flows out of the air galleries via the crack into the vacuum channel. The change of the pressure differential between the vacuum gallery and the air gallery resulting therefrom is measured as a signal carrier for the crack detection.

Up to this point, the air and vacuum channels have been produced on the sensor film using replica methods (casting methods) or using laser lithography. In the replica methods, a negative mold is firstly produced, which carries the vacuum and air galleries. A monomeric or oligomeric reaction mixture is then poured into the mold and hardened therein. The resulting positive is the CVM sensor—a plastic film which carries the vacuum and air galleries.

DE 10 2004 057 290 A1 describes an introduction of the vacuum and air galleries with the aid of laser lithography into the sensor substrate or the sensor film. The plastic or the polymer is vaporized by the laser beam because of the local heat introduction. The desired gallery pattern is introduced by appropriate lateral movement of the laser. The depth of the surface removal is controlled by the ratio of feed rate and laser intensity and by the number of laser passes. It is extremely difficult to set the required laser strength and the exact feed to set the depth of the galleries exactly. Multiple passes are frequently necessary to obtain the desired gallery shapes.

DESCRIPTION OF THE INVENTION

It is an object of the present invention to provide a sensor film which is suitable for the use of the comparative vacuum measurement method.

The object is achieved by a method for producing a sensor film and a sensor film for measuring cracks of a material surface using the comparative vacuum measurement method, a testing method for testing surface cracks of a component using the comparative vacuum measurement method, a usage of the sensor film for measuring cracks of a material surface using the comparative vacuum measurement method, and by an aircraft having a sensor film for measuring cracks of a material surface using the comparative vacuum measurement method having the features according to the independent claims.

According to an exemplary embodiment of the present invention, a method for producing a sensor film for measuring cracks of a material surface using the comparative vacuum measurement method is provided. A gallery having a predetermined gallery course is milled using a milling apparatus along a surface of the sensor film which has a plastic material.

According to a further exemplary embodiment, a sensor film for measuring cracks of a material surface using the comparative vacuum measurement method is provided, the sensor film being produced according to the above production method.

According to a further exemplary embodiment, a testing method for testing surface cracks of a component using the comparative vacuum measurement method is provided, a sensor film being used for the testing, which is produced using the above-mentioned production method. Firstly, an adhesive layer having an adhesive is applied to a sensor film surface. The sensor film is applied to a component surface. A vacuum atmosphere is provided in the gallery, a change of the vacuum atmosphere in the gallery being measured using a measuring device.

According to a further exemplary embodiment, the sensor film described above is used for measuring cracks of a material surface using the comparative vacuum measurement method.

According to a further exemplary embodiment, an aircraft having a sensor film described above is provided for measuring cracks of a material surface using the comparative vacuum measurement method.

Using the production method of the sensor film, instead of complex and costly laser technologies, a milling apparatus or a micro-milling apparatus may generate a predetermined gallery course along the sensor film surface, so that a desired pattern of galleries having a predetermined gallery depth arises on the sensor surface. The material-removing method for producing the galleries using milling allows a more rapid and cost-effective production possibility of the galleries in comparison to laser ablation. This is because the operational and provision costs of a laser system are high in comparison to a milling or micro-milling apparatus. In addition, a higher time outlay is required for the laser ablation, because the depth of the galleries must be executed by a complex controller in regard to greatly varying parameters. Thus, to achieve a specific depth of a gallery, feed rate must be oriented extremely precisely in connection with the laser intensity to achieve the gallery depth. To achieve a predetermined depth or width of the galleries, the laser sometimes has to pass through the gallery course multiple times, so that the desired result is achieved. Using the milling apparatus, the desired gallery depth and width may be achieved with only one pass, in that, for example, the milling head is exactly oriented accordingly. Therefore, production time and costs may be saved.

Furthermore, it is advantageous if the edges of the gallery walls are implemented as extremely smooth, to thus set the tightness between the component surface and the sensor film and to be able to thus measure a possible air exchange and/or extremely small cracks in the surface. In laser ablation, course-grain vaporization products from the ablation process typically condense on the edges of the gallery walls. Using the production method having micro-milling, smoother edges of the gallery wall may be achieved than with laser ablation. This results in significantly more reliable measurement.

The term "gallery" is understood as a groove and/or a channel or a through groove which varies in its depth or penetrates through the material of the sensor film. A defined width of the gallery of 100 to 250 micrometers may be provided using micro-milling.

According to a further exemplary embodiment, the sensor film is laid on a vacuum table and a vacuum is generated on the vacuum table to fasten the sensor film. The sensor film may thus be fastened extremely precisely and carefully for the processing or milling. Without further aids, the sensor film may be fastened solely by the resulting partial vacuum, without causing deformation of the sensor film during the processing.

According to a further exemplary embodiment, the milling apparatus is set up to mill the gallery using high-speed milling, the milling apparatus having a speed of 19,000 to 21,000 revolutions per minute (rpm). The smoothness of the gallery walls may be improved with increasing speed, so that a more exact measurement of cracks may be performed later. Only one manufacturing pass is necessary to achieve the smoothness.

According to a further exemplary embodiment, the sensor film is first tempered before the initial milling at a first temperature for a first time interval. Subsequently, the sensor film is cooled to an ambient temperature for a second time interval. Plastics may have improved structural properties for the milling because of the tempering. Tempering means that a solid body is heated to a temperature below the melting temperature. This is performed at a first temperature and in a first time interval, structural defects being compensated for and the short-range and long-range order attempting to reach lower free enthalpy. After the heating and/or the tempering at the first temperature for the first time interval, the sensor film is slowly cooled to the ambient temperature for a second time interval. Because plastics are often quite tough, improved machinability of the plastic and thus improved machinability may be achieved by the tempering. As a result of the tempering, there is material hardening of the plastic and thus a reduction of the toughness. This reduction of toughness of the plastic is to be attributed to the partial crystallization process of the plastic or the polymers caused by the tempering. Therefore, a material property of the plastic, such as the toughness or the warpage may be improved, so that the further processing is significantly simplified and improved.

According to a further exemplary embodiment, the sensor film is tempered at the first temperature at approximately 280° to 320° and for a first time interval of 8 to 12 minutes.

According to a further exemplary embodiment of the present invention, the gallery is milled into the sensor plate at a predefined depth. A predefined depth may be set using the milling. The predefined depth may be 25 to 100 micrometers depending on the thickness of the sensor plate. In comparison to the gallery generation by laser ablation, a predefined depth may be set using the milling method and the depth of the gallery may be abraded using one pass, for example. Multiple repetitions are not necessary, so that a gallery may be generated in the sensor film extremely rapidly and cost-effectively.

According to a further exemplary embodiment, a gallery is milled in such a way that a through channel having the predetermined gallery course is formed along the sensor film. A sealing layer is subsequently applied to one side of the through channel. After application of the sealing layer on one side of the through channel, a gallery which has a depth corresponding to the thickness of the sensor film is also obtained. During formation of a through channel, a specific predefined depth does not have to be ensured, but rather a through channel may simply be milled without consideration of the depth. Therefore, time and costs may be saved, because consideration does not have to be taken of a predetermined depth.

According to a further exemplary embodiment of the present invention, the milling chips arising upon milling are blown off during the milling using a blowing nozzle and the sensor film is cooled during the milling using the blowing nozzle. Because high speeds and rapid feed rates are used during milling, high temperatures arise. In addition, the milling chips must be removed from the machining area to achieve a smooth gallery wall. Using the blowing nozzle, a milling chip may be removed directly at the machining point and the sensor film may be cooled, so that extremely rapid speeds and feed rates are made possible.

According to a further exemplary embodiment, the milling chips arising upon milling are blown off using a suction apparatus. Furthermore, the sensor film is cooled during the milling using the suction apparatus. The suction apparatus generates a suction air flow which removes the milling chips and cools the sensor film using the resulting suction flow, so that extremely rapid speeds and feed rates may be used.

According to a further exemplary embodiment, a surface seal, in particular a metal varnish lacquer seal, is applied in the gallery. The smoothness of the gallery walls may thus be increased, so that improved measurement of cracks formation of a component surface may be achieved. The metal varnish lacquer seal may have silver zapon, for example. According to a further exemplary embodiment, a further gallery having a further predetermined gallery course is introduced along a surface of the sensor film using the milling apparatus. Therefore, a plurality of galleries and/or further galleries may be milled on the sensor film. In later use, a vacuum or a partial vacuum may be connected to one gallery and an atmospheric pressure may be connected to the further gallery, so that crack formation may be measured. The closer together the galleries and the further galleries lie, the better or the smaller cracks may be measured. Extremely fine and/or extremely narrow galleries may be generated or milled using the milling, which allow an extremely small gallery distance to be provided on the sensor film, so that the measurement of cracks on a component surface may be improved.

According to a further exemplary embodiment, the further gallery having the further predetermined gallery course is milled parallel to the predetermined gallery course of the gallery. It is thus ensured along a specific gallery pattern that any type of cracks on an area to be examined may be measured.

According to a further exemplary embodiment, the sensor film is fastened on the vacuum table using an adhesive tape. The sensor film may thus be clamped more solidly to a table to prevent displacement during milling.

According to a further exemplary embodiment, the plastic material is a polyimide material. Polyimide is a thermoplastic or a duroplastic high-performance plastic from the group of polyimides. A polyimide may be produced in the form of a film.

According to a further exemplary embodiment, the predetermined gallery course may be selected from the group consisting of linear and curved gallery courses. Because the gallery course is e.g. linear, curved, or a mixture of linear and curved gallery courses, a measuring area of the component to be examined may be covered using the pattern of gallery courses thus provided in such a way that nearly any crack propagation direction may be measured. The measuring reliability of the sensor film may thus be significantly improved.

According to a further exemplary embodiment, a predetermined gallery shape may be milled into the gallery using a boring-milling tool of the milling apparatus. Using a specific forming cutter or boring-milling tool, the galleries may have a conical, triangular, round, or rectangular shape in cross-section.

The embodiments of the production method apply for the sensor film, the testing method, the use, and for the aircraft and vice versa.

According to a further exemplary embodiment of the testing method, ambient air is applied to a further gallery, the ambient air of the further gallery being able to enter the vacuum gallery along a crack of the component. A change of the vacuum atmosphere in the gallery is measured using the measuring device. The air from the further galleries may thus penetrate along a crack of the component into the gallery having the vacuum atmosphere, so that a pressure change may be measured.

According to a further exemplary embodiment, the adhesive is laminated on. In contrast to the spray-on method of the adhesive, the galleries remain free of adhesive with lamination, i.e., for example, the application of adhesive using a painting method or an adhesive film, so that no restriction of the measurement results because of the adhesive.

According to a further exemplary embodiment, the adhesive is sprayed on. An adhesive layer may be applied rapidly using spraying.

According to a further exemplary embodiment of the testing method, the sensor film is rolled onto the component using an electrical rolling device. The sensor film may thus be rolled onto the component uniformly and at a uniform predetermined pressure, so that no leaks arise between the gallery and the environment, so that an air exchange may solely arise between the galleries through a crack of the component surface.

According to a further exemplary embodiment of the usage, the sensor film is used in an aircraft. High safety requirements for the structural monitoring and/or the structural health monitoring exist especially in aircraft, in which a high safety standard must be ensured. Therefore, a crack examination must also be performed at inaccessible points, such as in the kerosene tanks or other containers. By applying the sensor film, which may remain permanently installed, examination of the component services for cracks is possible at any time, without long equipping times of the testing configuration being necessary.

BRIEF DESCRIPTION OF THE DRAWINGS

In the following, exemplary embodiments are described in greater detail with reference to the attached drawings for further explanation and better understanding of the present invention.

DETAILED DESCRIPTION OF EXEMPLARY EMBODIMENTS

Identical or similar components in different figures are provided with identical reference signs. The illustrations in the figures are schematic and are not to scale.

Figure 2:
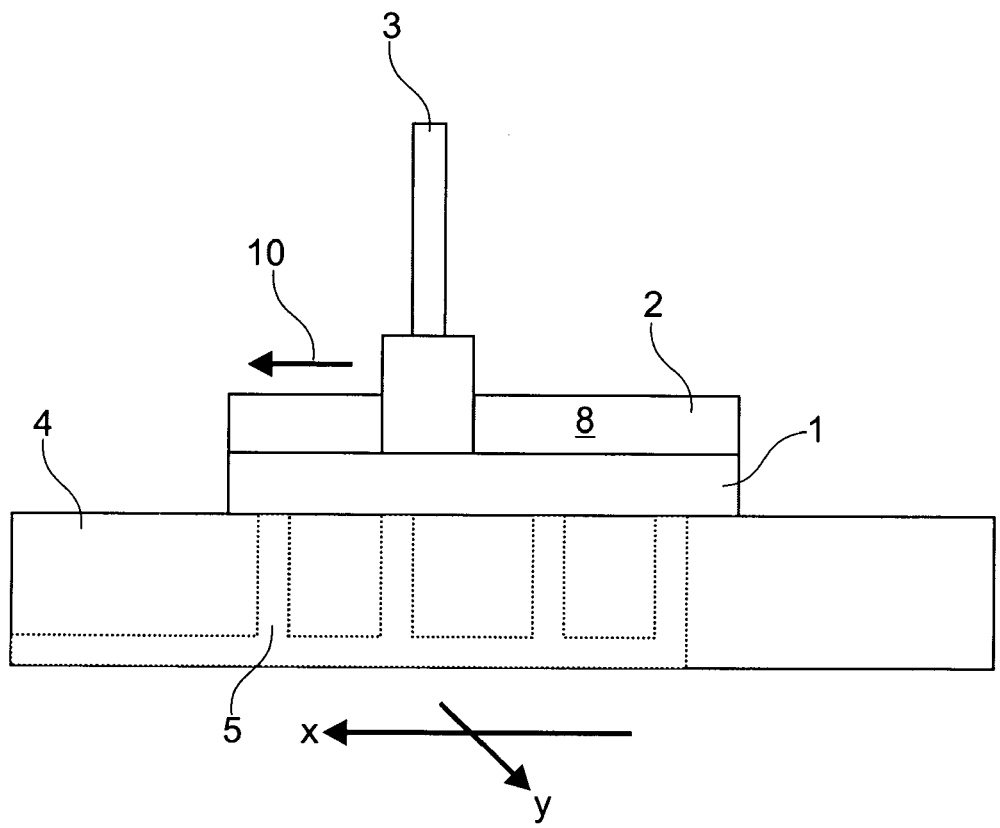
FIG. 2 shows a schematic illustration of a production configuration according to an exemplary embodiment of the present invention.

FIG. 2 shows an exemplary embodiment of the production configuration, by means of which a sensor film 1 may be produced according to the production method according to the present invention. A gallery 2 having a predetermined gallery course is milled along a surface of the sensor film 1 using a milling apparatus 3. The sensor film 1 has a plastic material.

Figure 1:
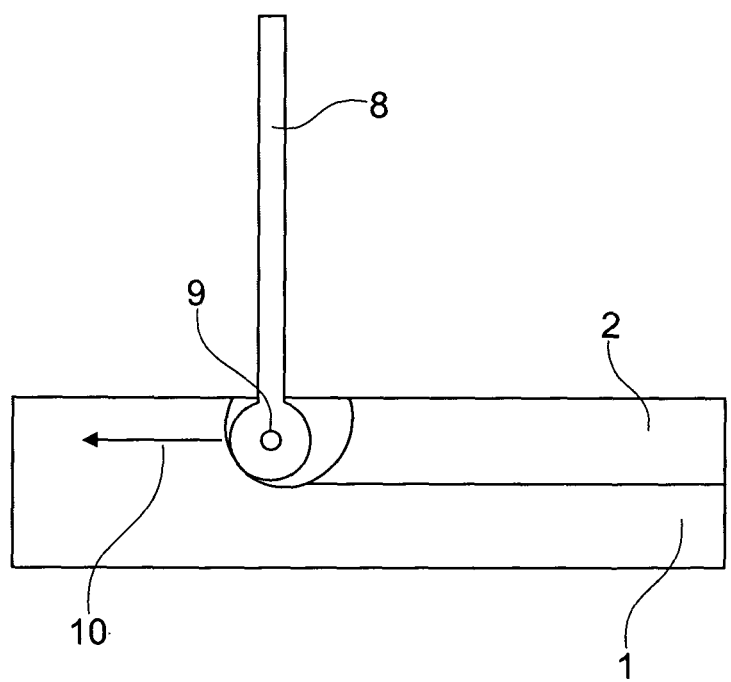
FIG. 1 shows a schematic illustration of a production device for a sensor film as it is known from the prior art.

FIG. 1 shows a well-known production configuration for producing a sensor film for the comparative vacuum measurement method. Using a laser 8, a gallery 2 is introduced into a sensor material 1 in a vaporization zone 9 because of the heat thus arising. The laser 8 moves along the feed direction 10. To obtain a predetermined depth of the gallery 2, the velocity in the feed direction 10 and the laser intensity of the laser 8 must be set exactly or a specific depth must be achieved by multiple passes of the laser over the sensor film 1.

FIG. 2 shows a device, by means of which an exemplary embodiment of the method may be executed. A boring-milling tool 3 may mill a gallery 2 in the sensor film 1 using a feed 10. Furthermore, the sensor film 1 may be fastened on a vacuum table, which has vacuum channels 5. The sensor film 1 may be fastened carefully by generating a vacuum of the vacuum table 4, so that the sensor film 1 is not displaced during the milling procedure, i.e., during the feed 10, of the boring-milling tool 3. The boring-milling tool 3 is movable on a surface at a specific height. Any shape of the galleries 2 may be generated using free mobility in the X and Y directions of the boring-milling tool 3.

Figure 3:
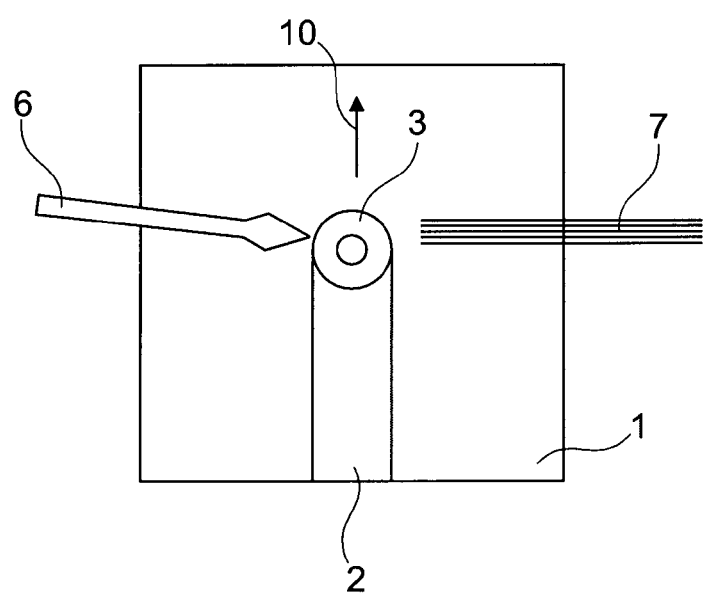
FIG. 3 shows a schematic illustration of an exemplary embodiment of a production configuration having a blowing nozzle and a suction device according to an exemplary embodiment of the present invention.

FIG. 3 shows a top view of the production configuration for a sensor film for measuring cracks of a metal surface using the comparative vacuum measurement method. A boring-milling tool 3 is movable along the feed 10 and may thus apply a gallery 2 to the sensor film 1. The sensor film 1 may be cooled using a blowing nozzle 6 and/or a suction device 7, so that the plastic material of the sensor film 1 does not vaporize or become too hot. The milling chips of the sensor film 1 may be removed from the processing area using the blowing nozzle 6 or the suction device 7.

Higher speeds may be used because of the cooling of the blowing nozzle 6 or the suction device 7, such as 18,000 to 22,000 revolutions per minute (rpm), or a more rapid feed 10 may be implemented.

Figure 4:
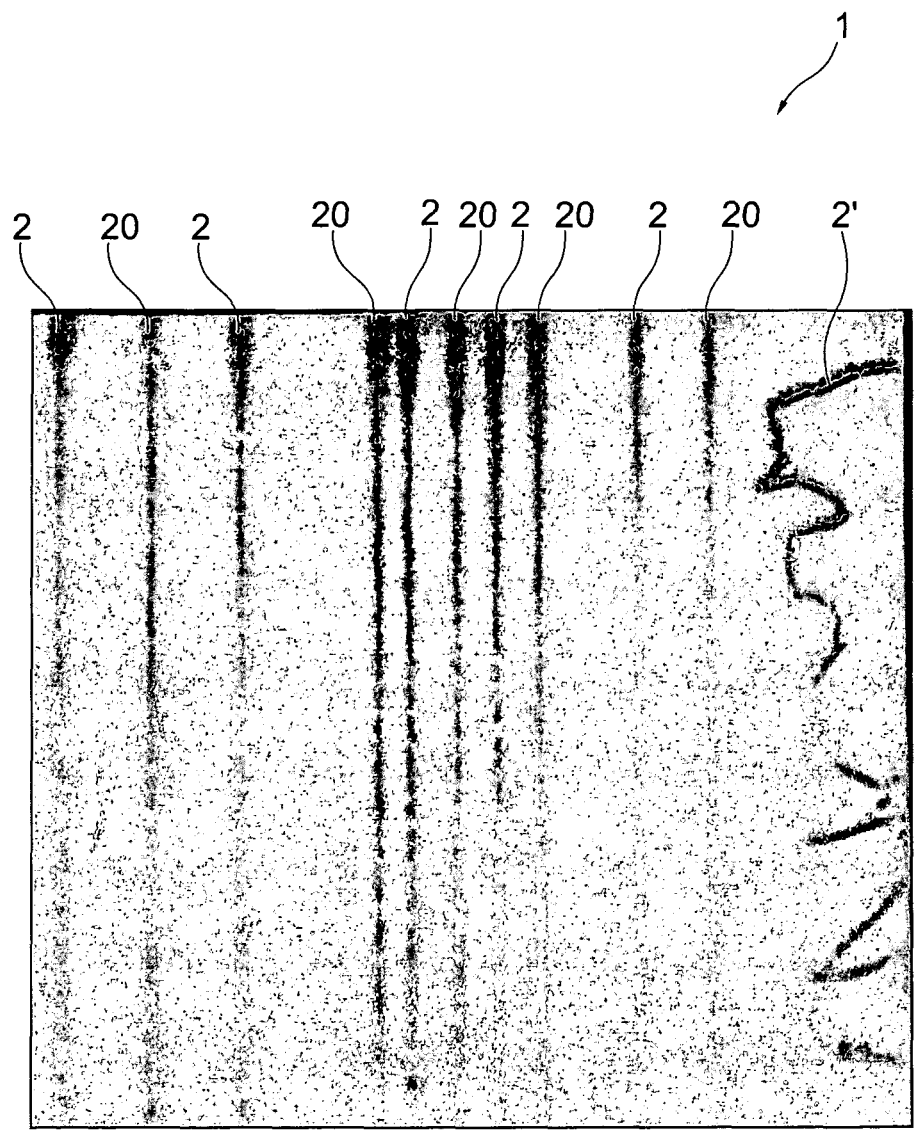
FIG. 4 shows a schematic illustration of a sensor film having multiple galleries according to an exemplary embodiment.

FIG. 4 shows a sensor plate 1 having multiple galleries 2 and further galleries 20. The further galleries 20 may be filled with ambient air and the galleries 2 with a vacuum atmosphere, for example. The sensor film 1 is laid on a component surface. If a crack is located on the component surface, a pressure exchange may arise along a crack between the vacuum gallery 2 and the ambient gallery 20. This pressure exchange is measurable, so that a surface crack may be concluded.

Furthermore, a gallery 2' is shown, which represents a nonlinear gallery course. Therefore, all different gallery shape courses may be provided using the milling method.

Figure 5:
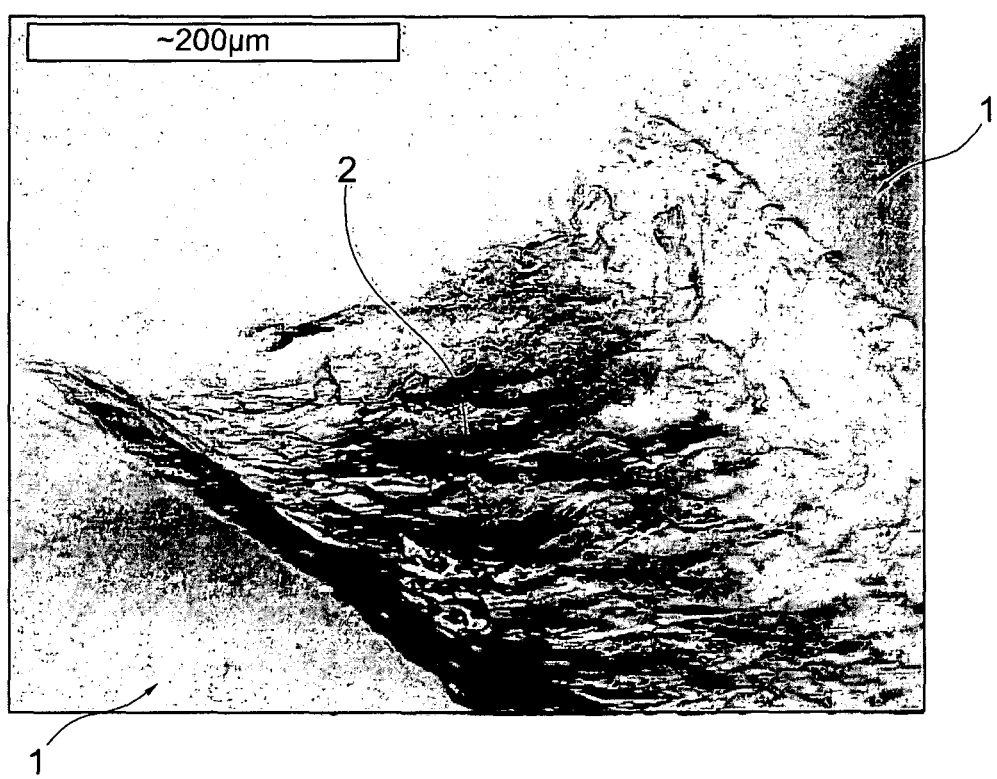
FIG. 5 shows a microscopic picture of a milled gallery according to an exemplary embodiment.

FIG. 5 shows a microscopic picture of a milled gallery 2 in a sensor film 1. The width of the gallery 2 is approximately 25 micrometers. At a milling speed of approximately 20,000 revolutions per minute (rpm), a smoother gallery surface may be obtained in comparison to typical laser ablation, which is recognizable under the microscope.

Moreover, it is to be noted that "comprising" does not exclude other elements or steps and "a" or "one" does not exclude multiples. Furthermore, it is to be noted that features or steps which have been described with reference to one of the above exemplary embodiments may also be used in combination with other features or steps of other exemplary embodiments described above. Reference signs in the claims are not to be viewed as a restriction.

LIST OF REFERENCE SIGNS

1 sensor film
2 gallery
3 milling apparatus
4 vacuum table
5 vacuum line
6 blowing nozzle
7 suction device
8 laser
9 vaporization zone
10 feed direction
20 further gallery

The invention claimed is:

1. A method for producing a sensor film for measuring cracks in a material surface using a comparative vacuum measurement method,
the method for producing the sensor film comprising:
applying a sensor film comprising a plastic material on a tempering surface;
hardening the sensor film by tempering the sensor film at a first temperature for a first time interval;
cooling the tempered sensor film for a second time interval to an ambient temperature; and
milling at least one first gallery having a first predetermined gallery course along a surface of the sensor film using a milling apparatus.

2. The method according to claim 1, further comprising:
applying the sensor film on a vacuum table; and
generating a vacuum to fasten the sensor film on the vacuum table.

3. The method according to claim 1,
wherein the milling apparatus mills the at least one first gallery using high-speed milling;
wherein a speed of the milling apparatus is 19,000 to 21,000 rpm.

4. The method according to claim 1, wherein
the first temperature is from about 280° C. to about 320° C. and the first time interval is from about 8 minutes to about 12 minutes.

5. The method according to claim 1, wherein
milling the gallery occurs in such a way that a through channel having a predetermined gallery course is formed along the sensor film, the method further comprising
applying a sealing layer on one side of the through channel.

6. The method according to claim 5 further comprising applying a sealing layer on one side of the through channel.

7. The method according to claim 1, further comprising:
blowing off milling chips from the sensor film arising during milling using a blowing nozzle; and
cooling the sensor film during the milling using the blowing nozzle.

8. The method according to claim 1, further comprising:
removing milling chips arising during milling using a suction apparatus; and
cooling the sensor film during the milling using the suction apparatus.

9. The method according to claim 1, further comprising:
applying a surface seal, selected from the group consisting of a metal varnish and a lacquer seal, in the gallery.

10. The method according to claim 1, further comprising:
milling a second gallery having a second predetermined gallery course along a surface of the sensor film using the milling apparatus.

11. The method according to claim 10,
wherein the second gallery having the second predetermined gallery course is milled parallel to the first predetermined gallery course of the at least one first gallery.

12. The method according to claim 1,
wherein the plastic material comprises a polyimide material.

13. The method according to claim 1,
wherein the first predetermined gallery course is selected from the group consisting of linear and curved gallery courses.

14. The method according to claim 1, wherein
milling the first predetermined gallery shape of the at least one first gallery is accomplished using a boring-milling tool of the milling apparatus.

15. A sensor film for measuring cracks of a material surface using the comparative vacuum measurement method,
wherein the sensor film is produced by a method comprising:
applying a sensor film comprising a plastic material on a tempering surface;
hardening the sensor film by tempering the sensor film at a first temperature for a first time interval;
cooling the tempered sensor film for a second time interval to an ambient temperature; and
milling at least one first gallery having a first predetermined gallery course along a surface of the sensor film using a milling apparatus.

16. A testing method for testing surface cracks of a component using the comparative vacuum measurement method,
wherein a sensor film produced using a production method, is used for the testing;
wherein the testing method comprises:
applying an adhesive layer having an adhesive to a sensor film surface;
applying the sensor film to a component surface;
providing a vacuum atmosphere in the gallery; and measuring a change of the vacuum atmosphere in the gallery using a measuring device; and wherein the production method comprises:
  applying a sensor film comprising a plastic material on a tempering surface;
  hardening the sensor film by tempering the sensor film at a first temperature for a first time interval;
  cooling the tempered sensor film for a second time interval to an ambient temperature; and
  milling at least one first gallery having a first predetermined gallery course along a surface of the sensor film using a milling apparatus.

17. The testing method according to claim 16, further comprising
  applying ambient air to the second gallery.

18. The testing method according to claim 16,
  wherein the adhesive is laminated on the sensor film.

19. The testing method according to claim 16,
  wherein the adhesive is sprayed on the sensor film.

20. The testing method according to claim 16, further comprising:
  rolling the sensor film onto the component using an electrical rolling device.

21. An aircraft comprising a sensor film for measuring cracks in a material surface using a comparative vacuum measurement method, wherein the sensor film is produced by a method comprising:
  applying a sensor film comprising a plastic material on a tempering surface;
  hardening the sensor film by tempering the sensor film at a first temperature for a first time interval;
  cooling the tempered sensor film for a second time interval to an ambient temperature; and
  milling at least one first gallery having a first predetermined gallery course along a surface of the sensor film using a milling apparatus.

* * * * *

UNITED STATES PATENT AND TRADEMARK OFFICE
CERTIFICATE OF CORRECTION

PATENT NO. : 8,490,473 B2  
APPLICATION NO. : 12/444727  
DATED : July 23, 2013  
INVENTOR(S) : Clemens Bockenheimer and Peter Kohl Page 1 of 1

It is certified that error appears in the above-identified patent and that said Letters Patent is hereby corrected as shown below:

Title Page, Item (12) "Bokenhelmer" should read --Bockenheimer--.

Title Page, Item (75) replace "Bockenhelmer" with --Bockenheimer--.

Signed and Sealed this  
Eighth Day of April, 2014

Michelle K. Lee  
*Deputy Director of the United States Patent and Trademark Office*